| United States Patent [19] | [11] | 4,434,244 |
|---|---|---|
| Kuhlmann et al. | [45] | Feb. 28, 1984 |

[54] MALEIC ANHYDRIDE CATALYST RECYCLE

[75] Inventors: George E. Kuhlmann, Naperville; Stephen V. Hoover, Aurora, both of Ill.

[73] Assignee: Standard Oil Company (Indiana), Chicago, Ill.

[21] Appl. No.: 385,794

[22] Filed: Jun. 7, 1982

[51] Int. Cl.$^3$ ............................................. B01J 27/14
[52] U.S. Cl. ................................. 502/209; 502/210; 502/211
[58] Field of Search ................... 252/435, 437; 423/64

[56] References Cited

U.S. PATENT DOCUMENTS

| 3,293,268 | 12/1966 | Bergman et al. | 549/259 |
|---|---|---|---|
| 3,832,359 | 8/1974 | Freerks et al. | 549/260 |
| 3,867,411 | 2/1975 | Roffelson et al. | 549/260 |
| 3,888,886 | 6/1975 | Young et al. | 549/260 |
| 4,002,650 | 12/1977 | Bremer et al. | 549/260 |
| 4,147,661 | 4/1979 | Higgins et al. | 252/437 X |
| 4,149,992 | 4/1979 | Mount et al. | 252/437 X |
| 4,151,116 | 4/1979 | McDermott | 252/437 X |
| 4,152,338 | 5/1979 | Kerr | 549/260 |
| 4,152,339 | 5/1979 | Kerr et al. | 549/260 |
| 4,251,390 | 2/1981 | Barone | 252/435 |
| 4,283,288 | 8/1981 | Udovich et al. | 252/435 X |
| 4,294,722 | 10/1981 | Bremer et al. | 252/435 |
| 4,359,405 | 11/1982 | Mount et al. | 252/437 X |

*Primary Examiner*—William G. Wright
*Attorney, Agent, or Firm*—Gunar J. Blumberg; William T. McClain; William H. Magidson

[57] ABSTRACT

A catalyst for the oxidation of hydrocarbons comprising a phosphorus and vanadium mixed oxide wherein the catalyst prepared by using an organic medium can be recycled according to our process thus conserving up to ninety percent of the vanadium used in the preparation of the catalyst. The mixed oxide can also be promoted by a transitional element of the IV and V period of the periodic table. These catalysts are particularly useful for the oxidation of $C_4$ hydrocarbons to maleic anhydride.

12 Claims, No Drawings

MALEIC ANHYDRIDE CATALYST RECYCLE

BACKGROUND OF THE INVENTION

1. Field of the Invention

The field of this invention relates to the recycle of phosphorus-vanadium-oxide catalysts prepared in an organic medium thus conserving up to ninety percent of the vanadium. These catalysts can be promoted by a transition element of the IV and V period of the periodic table. These catalysts are useful for the manufacture of maleic anhydride from n-butane.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butane is well known and until recently, the principal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339 and British Application No. 2,019,839A. While the aforementioned prior art tends to bring about some improvement in the performance of the phosphorus vanadium catalyst there remains much room for improvement, particularly from the standpoint of high conversion, yield and catalyst life.

The manufacture of phosphorus-vanadium-oxide catalysts in an organic medium leaves economically significant quantities of vanadium, phosphorus and catalyst components dissolved in the mother liquor. In the event co-metal is used, significant quantities of the co-metal are also dissolved in the mother liquor. The co-metals include zinc, molybdenum, zirconium, niobium, cerium, chromium, manganese, nickel and uranium. About one third of the most expensive catalyst ingredient, vanadium, remains in the mother liquor. It is an object of this invention to recover the catalyst material remaining in the mother liquor and then reuse it in the manufacture of additional quantities of the phosphorus-vanadium-oxide catalyst useful for the oxidation of butane to maleic anhydride. Thus saving ninety percent of the vanadium, the most expensive component of the maleic anhydride catalyst. Suitable the phosphorus vanadium catalysts are promoted by a transition element of the IV and V period of the periodic table. Suitable promoters include molybdenum, zinc, zirconium, niobium, cerium, chromium, manganese, nickel, and uranium.

Surprisingly, it is found that the catalytic material found in the residue may be directly reapplied to prepare another fresh phosphorus-vanadium-oxide catalyst or the fresh phosphorus vanadium oxide-promoted catalyst without any deleterious effect on the catalyst activity.

The recycled catalyst comprises a phosphorus-vanadium mixed oxide. The atomic ratio of the vanadium to phosphorus can suitably be in the range of about 1.0:1.0 to about 0.50:1.0, preferably in the range of about 0.90:1.0 to about 0.60:1.0. In the event a promoter is employed, the total atomic ratio of the promoter to vanadium advantageously is in the range of about 0.001:1 to about 0.100:1. It is preferred that the total atomic ratio of a promoter such as molybdenum, zinc, zirconium, niobium, cerium, chromium, manganese, nickel and uranium to vanadium should be in the range of about 0.01:1 to about 0.05:1. The atomic ratio of phosphorus to vanadium is suitably in the range of about 1.00:1 to about 1.90:1, preferably about 1.10:1 to about 1.70:1.

Catalysts recycled according to the invention may be made from an organic solvent system wherein vanadium pentoxide in the presence of the promoter is reduced with gaseous hydrogen chloride. Subsequent reaction of the vanadium-promoter oxide solution with orthophosphoric acid and removal of water of reaction by azeotropic distillation result in precipitation of a crystalline vanadium-phosphorus mixed oxide or the vanadium-phosphorus-promoter mixed oxide which may suitably be filtered from the mother liquor, dried and then employed as an oxidation catalyst for the manufacture of maleic anhydride from butane feedstock. Suitably, organic solvents are alcohols or mixtures of alcohols with aromatic hydrocarbons such as benzene and orthoxylene. Aliphatic alcohols are usually employed in the process and isobutanol is the preferred alcohol. The precipitation of the phosphorus-vanadium-oxide complex or the phosphorus-vanadium-promoter oxide is achieved by reducing the solubility of this complex in solution by employing a co-solvent. Precipitation can also be effected by reducing the temperature and removal of the solvent. The use of a co-solvent such as benzene or orthoxylene also functions to facilitate removal of excess water through azeotropic distillation. Precipitation of the phosphorus-vanadium-mixed oxide can suitably be effected by azeotropic distillation of the organic solvent and the water of reaction and subsequent evaporation of the organic solvent. The promoter may be added as a compound together with vanadium or separately. In the event the promoter is molybdenum or zinc, suitable molybdenum or zinc compounds comprise metallic molybdenum or zinc, molybdenum chloride, zinc chloride, molybdenum oxide, zinc oxide and most soluble molybdenum salts and zinc salts. The mother liquor from the preparation of these catalysts can be recycled and additional reactants added to form a new catalyst. Surprisingly this catalyst prepared from the mother liquor has the same activity as a new catalyst, yet by using the recycle process, up to 90 percent of the vanadium is recovered.

According to our process, the average valence of vanadium is in the range of about +3.8 to about +4.5. In the catalyst preparation according to our recycle of the mother liquor, various anhydrous phosphoric acids may be used including ortho-phosphoric, pyrophosphoric, triphosphoric or meta-phosphoric acid. The vanadium compound can be vanadium pentoxide, vanadium tetrachloride, vanadium trichloride, vanadium oxydichloride, vanadium oxytrichloride, vanadium tetroxide, vanadium oxalate, and most soluble vanadium complexes. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium-containing acids such as meta-vanadic acid, pyrovanadic acid and the like; vanadium salts such as ammonium meta-vanadate, vanadium sulfate, vanadium phosphate, vanadyl formate, vanadyl oxalate and the like. However, vanadium pentoxide is preferred.

This invention also comprises a process for oxidizing butane to maleic anhydride by contacting it in the presence of oxygen with the phosphorus-vanadium-oxide catalyst or the phosphorus-vanadium promoter oxide catalyst prepared from the mother liquor. The oxidation of butane to maleic anhydride may be accomplished by contacting n-butane in low concentration in oxygen with the described catalyst. Air is entirely satisfactory as a source of oxygen, but synthetic manufactures of oxygen and diluent gases such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite-potassium nitrate eutectic constant temperature mixture. An additional method of temperature control is to use a metal block reactor whereby the metals surrounding the tube act as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a heat preheat zone under an inert material such as one-quarter inch Alundum pellets, inert ceramic balls, nickel balls, or chips, and the like present at about one-half to one-tenth the volume of the active catalyst present.

The temperature of reaction may be varied within some limits but, normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°-50° F. above the salt bath temperature. The temperature of the reactor, of course, will also depend to some extent upon the size of the reactor and the butane concentration.

The reaction may be conducted at atmospheric, superatmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these samples are given for illustrative purposes only and will not be interpreted as limiting the invention in any way. In the examples the terms "conversion", "selectivity" and "yield" are defined as follows:

$$\text{Conversion \%} = \frac{\text{Moles hydrocarbon reacted}}{\text{Moles hydrocarbon in feed}} \times 100$$

$$\text{Selectivity \%} = \frac{\text{Moles maleic produced}}{\text{Moles hydrocarbon feed consumed}} \times 100$$

$$\text{Yield Wt. \%} = (\text{Conversion}) \times (\text{Selectivity}) \times 1.69$$

EXAMPLE 1

Catalyst Preparation

The reaction vessel was a 12-liter, round-bottomed, four-necked flask fitted with a mechanical stirrer, gas dispersion tube, a condenser, and a thermowell. To this flask were added 3000 ml of isobutyl alcohol, 728 g of $V_2O_5$ (8 mole of V) and 34.6 g of MoO (0.24 mole of Mo). Over a period of 25 hours, gaseous HCl reduced the vanadium at 65° C. Then 960 g of $H_3PO_4$ (9.8 mole of P with $H_3PO_4$ 98–100 percent pure) and 1000 ml of o-xylene were added and the mixture refluxed at up to 106° C. for 17 hours to remove azeotrope. The mixture P/V/Mo atomic ratio was 1.22 to 1.0 to 0.03. After filtration at 70° C., washing with fresh isobutyl alcohol and drying at 120° C. in a vacuum oven, 1290 g of dry catalyst (66 mole percent yield based on vanadium charged) were obtained. The catalyst had a P/V/Mo atomic ratio of 1.68 to 1 to 0.017.

EXAMPLE 2

3571 g of mother liquor (100 percent) from Example 1 were placed in the 12 liter flask. To this flask 476.5 g of $V_2O_5$ (5.2 moles of V) and 12.75 g of $MoO_3$ (0.09 moles of Mo) were added. After only 1½ hours, V reduction was complete and 860 g of $H_3PO_4$ (8.7 mole of P with $H_3PO_4$ 98–100 percent pure) and 1000 ml of o-xylene were added. The mixture refluxed for 17 hours at up to 106° C. to remove azeotrope. After drying, the catalyst weighed 1223 g (62 mole percent yield based on 5.2 moles of vanadium charged plus 2.6 moles of vanadium dissolved in the recycle mother liquor). The catalyst had a P/V/Mo atomic ratio of 1.64 to 1 to 0.018.

EXAMPLE 3

Catalyst Pilling and Activation

The catalyst powders were mixed with 5 weight percent Sterotex (a partially hydrogenated vegetable oil) and pilled as 3/16"×3/16" tablets. A catalyst activation process conditioned the uncalcined catalyst. Since pure air activation above 375° C. caused some undesirable vanadium oxidation to the +5 state, a 1.0 volume percent concentration of butane (a reducing gas) in air was used as the activation atmosphere to prevent excessive catalyst oxidation. The butane-air streams were passed through a water saturator at room temperature to provide about a 3 mole percent humidification level because the apparent removal of coke by the resulting steam of reaction temperatures caused up to a 10 weight percent maleic anhydride yield increase using this process modification. This catalyst activation process, shown in Table I, was designed to produce catalyst that was free of solvent, pilling aid, and other volatiles.

Once at 780° F., the catalyst reaction temperature would be gradually increased during the next two weeks to as high as 810° F. to obtain butane conversions near 90 mole percent. After this was achieved, the temperature would be reduced slowly to as low as 760° F. to increase maleic anhydride selectivity.

Analysis

The reactor effluents were analyzed by a Fisher-Hamilton Model 29 Gas Partitioner equipped with a dual detector system and a di-2-ethylhexyl sebacate column to resolve butane and carbon dioxide and a 13X Molecular Sieve column to resolve oxygen, nitrogen and carbon monoxide.

Calculations

The chromatogram peak areas were integrated and reported by a Spectra-Physics SP-4000 Data Processor. The gas chromatograph correction factors were checked daily by a Matheson primary standard reference gas mixture containing butane, CO, and $CO_2$ in synthetic air which itself has been checked against three primary standard reference binary mixtures (butane in nitrogen, CO in nitrogen, $CO_2$ in synthetic air).

Evaluation of Catalyst Performance

The performance of the maleic anhydride catalysts from the first series of recycle is shown in Graphs I and II. The original preparation (Example 1–95) and first recycle catalyst (Example 1–97) exhibited excellent activity, the second recycle catalyst (Example 1–99) and the third recycle catalyst (Example 1–101) also produces an acceptable catalyst. Their selectivity to maleic anhydride has remained near 60 mole percent, but their conversion of butane settled to 50–70 mole percent. The catalyst activity declines with each recycle.

As illustrated in Table II, the o-xylene content of the mother liquors from the second and third recycle was quite high. Although this did not affect the amount of catalyst precipitated, it may have altered catalyst characteristics such as surface properties. When we attempted to conduct another recycle with a very low concentration of o-xylene in the mother liquor (Catalysts Example 1–111 and −115) the amount of precipitate recovered was reduced by one-half. Consequently, we have concluded that the o-xylene concentration should be within the range of 15–35 weight percent. More complete data are contained for all the recycle runs in Table III. This data has shown that consistency was obtained in catalyst yield and composition:

1. On a 5-pound preparation scale basis, all catalyst yields were within a 2274–2564 gram (5.0–5.64 pound) range.
2. With a stirring P/V/Mo atomic ratio of 1.22 to 1 to 0.03, we have always found the catalyst P/V/Mo atomic ratio to be 1.51±0.11 to 1 to 0.015±0.003 and the mother liquor P/V/Mo atomic ratio to be 0.46±0.13 to 1 to 0.06±0.01 (ave. dev.).

As shown by the data in Table III the following experimental conditions have been discovered which yield high-performance maleic anhydride catalysts.

1. 0–100 percent of the mother liquor may be recycled directly to the next catalyst preparation.
2. Reduction of the vanadium with HCl gas may proceed normally at 65° C.±2° C.
3. Immediately upon the cessation of vanadium reduction (as indicated by a loss of 65° C. reaction temperature) the addition of 98–100 percent pure $H_3PO_4$ (prepared at 40° C. by adding $P_2O_5$ slowly to 85 percent $H_3PO_4$) and o-xylene may proceed.
4. Maximum reflux temperature should be 104°–105° C. at which time the mother liquor should contain less than 4.0 weight percent $H_2O$ and about 15–35 weight percent o-xylene.
5. Catalyst filtration at 60°–70° C., washing with isobutyl alcohol until a clear filtrate appears should be followed by drying in a vacuum oven.

TABLE I

| Maleic Anhydride Catalyst Activation Process | | |
|---|---|---|
| Atmosphere: | Humidified 1 Vol percent Butane-Air Stream at 1.4 Weight Hourly Space Velocity | |
| Temperature | Time | Results |
| 340° F. | 2 Hours | Removed Isobutyl Alcohol Solvent |
| 350 650° F. | 2 Hours | Removed Sterotex Pilling Aid |
| 650° F. | 2–16 Hours | Removed Sterotex Pilling Aid |
| 650 780° F. | 30° F./Hour | Removed Water of Crystallization |
| 780° F. | 24 Hours | Catalyst Conditioning |

TABLE II

| Effect of o-Xylene Concentration on Maleic Anhydride Catalyst Synthesis | | |
|---|---|---|
| Recycle | Number 1-A | Number 1-B |

TABLE II-continued

Effect of o-Xylene Concentration on Maleic Anhydride Catalyst Synthesis

| Catalyst Prepared in Example 1 | 95 | 97-3 |
|---|---|---|
| Concentration of o-xylene in catalyst mother liquor, weight percent | 34 | 41 |
| Maleic Anhydride catalyst precipitate, gms.* | 1290 | 1223 |
| Catalyst activity | Excellent | Excellent |

| Recycle | Number 1-C | Number 1-D |
|---|---|---|
| Catalyst Number Example 1 | 99-1 | 101-1 |
| Concentration of o-xylene in catalyst mother liquor, weight percent | 61 | 54 |
| Maleic Anhydride catalyst precipitate, gms. | 1266 | 1150 |

| Recycle | Number 2-A | Number 2-B |
|---|---|---|
| Catalyst Number Example 1 | 111 | 115 |
| Concentration of o-xylene in catalyst mother liquor, weight percent | 14 | 7.9 |
| Maleic Anhydride catalyst precipitate, gms. | 2491 | 1395 |

| Recycle | Number 3-A | Number 3-B |
|---|---|---|
| Catalyst Number Example 1 | 119 | 121 |
| Concentration of o-xylene in catalyst mother liquor, weight percent | 25% | 29 |
| Maleic Anhydride catalyst precipitate, gms. | 2564 | 2420 |

TABLE III

MALEIC ANHYDRIDE CATALYST SYNTHESIS WITH MOTHER LIQUOR RECYCLE

| Recycle Number | Preparation Number Example 1 | Amount of Mother Liquor Recycle | Precipitated Catalyst P/V/Mo Ratio* |
|---|---|---|---|
| 1-A | 95 | Base | 1.68/1/0.017 |
| 1-B | 97 | 100% | 1.64/1/0.018 |
| 1-C | 99 | 100 | 1.70/1/0.015 |
| 1-D | 101 | 100 | 1.77/1/0.026 |
| 2-A | 111 | Base | 1.55/1/0.009 |
| 2-B | 115 | 100 | 1.13/1/0.008 |
| 3-A | 119 | Base | 1.49/1/0.013 |
| 3-B | 121 | 90 | 1.69/1/0.014 |
| 3-C | 124 | 90 | 1.68/1/0.014 |
| 4-A | 128 | Base | 1.67/1/0.021 |
| 4-B | 131 | 50 | 1.42/1/0.011 |
| 4-C | 134 | 50 | 1.59/1/0.016 |
| 5-A | 137 | Base | 1.47/1/0.016 |
| 5-B | 139 | 75 | ND |
| 6-A | 143 | Base | 1.55/1/0.016 |
| 6-B | 145 | 75 | 1.64/1/0.017 |
| 6-C | 147 | 75 | 1.65/1/0.015 |

| Precipitated Catalyst Yield, g** | Mother Liquor Atomic P/V/Mo Ratio | Water Wt. % | o-Xylene Wt. % |
|---|---|---|---|
| 1290 (× 2 = 2580) | 0.37/1/0.05 | 1.60 | 34 |
| 1223 (× 2 = 2446) | 0.49/1/0.06 | 0.59 | 41 |
| 1266 (× 2 = 2532) | 0.44/1/0.06 | 0.49 | 61 |
| 1150 (× 2 = 2300) | 0.36/1/0.06 | 0.55 | 54 |
| 2491 | 0.74/1/0.04 | 1.0 | 14 |
| 1395 | 1.41/1/0.06 | 3.7 | 7.8 |
| 2564 | 0.49/1/0.08 | 2.24 | 25 |
| 2420 | 0.18/1/0.07 | 0.88 | 29 |
| 2235 | 0.20/1/0.06 | 1.08 | 32 |
| 2179 | 0.93/1/0.07 | 3 | 20 |
| 2402 | 0.72/1/0.10 | 3 | 24 |
| 2388 | 0.56/1/0.06 | 3 | 20 |
| 2461 | 0.59/1/0.06 | 3.3 | 17 |
| ND | ND | ND | ND |
| 2373 | 0.58/1/0.06 | 3.8 | 17 |
| 2349 | 0.44/1/0.05 | 3.7 | 26 |
| 2274 | 0.33/1/0.03 | 3.6 | 25 |

TABLE III-continued
MALEIC ANHYDRIDE CATALYST SYNTHESIS WITH MOTHER LIQUOR RECYCLE

| Reaction Conditions | | | Catalyst Maleic Anhydride Yield After Thirty Days (720 hours) on-Streams*** |
|---|---|---|---|
| HCl Reduction Time, Hours | Reflux Time, Hrs. | Maximum Temp. °C. | |
| 2.5 | 17 | 106 | 107 wt % |
| 1.5 | 17 | 106 | 90 |
| 1.0 | 17 | 106 | 68 |
| 2.0 | 17 | 124 | 48 |
| 4.0 | 44 | 108 | 83 |
| 4.5 | 21 | 103 | 91 |
| 5.0 | 22 | 103 | 90 |
| 4.0 | 18 | 100 | 88 |
| 3.3 | 20 | 120 | 77 |
| 5.0 | 17 | 102 | 88 |
| 5.5 | 30 | 104 | 79 |
| 6.0 | 21 | 104 | 98 |
| 5.0 | 20 | 104 | 93 |
| 24.0 | 0.1 | 85 | ND (no product) |
| 5.0 | 4 | 102 | 93 |
| 4.0 | 5 | 103 | 83 |
| 4.0 | 5 | 103 | 91 |

NA = Not Available
ND = Not Determined
*Starting P/V/Mo atomic ratios were 1.22 to 1 to 0.03
**The first four catalyst preparation were "Half-sized" and are shown with doubled catalyst yield to facilitate their comparison to other experiments.
***Nominal VHSV = 1000

We claim:

1. In a process for the production of phosphorus-vanadium-oxide catalyst in an organic reaction medium wherein the ratio of phosphorus to a vanadium is in the range of about 1.2:1 to about 1.8:1 the improvement comprising adding $H_3PO_4$ immediately after the vanadium reduction has terminated and recycling mother liquor comprising at least 15 weight percent ortho xylene remainder being orthophosphoric acid and aliphatic alcohol and thus recovering up to ninety percent of the vanadium.

2. The process of claim 1, wherein the aliphatic alcohol is isobutyl alcohol.

3. The process of claim 1, wherein the mother liquor comprises about 15 to about 35 weight percent orthoxylene.

4. In a process for the production of phosphorus-vanadium-oxide catalyst promoted by a transition element of the IV and V period of the periodic table in an organic reaction medium wherein the ratio of phosphorus to vanadium is in the range of about 1.2:1 to about 1.8:1 and the ratio of vanadium to the promoter is in the ratio of about 0.001 to about 1:0,10, the improvement comprising adding $H_3PO_4$ immediately after the vanadium reduction has terminated and recycling mother liquor comprising at least 15 weight percent ortho xylene remainder being orthophosphoric acid and aliphatic alcohol and thus recovering up to ninety percent of the vanadium.

5. The process of claim 4, wherein the aliphatic alcohol is isobutyl alcohol.

6. The process of claim 4, wherein the mother liquor comprises about 15 to 35 weight percent orthoxylene.

7. In a process for the production of phosphorus-vanadium-molybdenum oxide catalyst in an organic reaction medium wherein the ratio of phosphorus to vanadium is in the range of about 1.2:1 to about 1.8:1 and the ratio of vanadium to molybdenum is in the ratio of about 0.001 to about 1:0.10, the improvement comprising adding $H_3PO_4$ immediately after the vanadium reduction has terminated and recycling mother liquor comprising at least 15 weight percent ortho xylene remainder being orthophosphoric acid and aliphatic alcohol and thus recovering up to ninety percent of the vanadium.

8. The process of claim 7, wherein the aliphatic alcohol is isobutyl alcohol.

9. The process of claim 7, wherein the mother liquor comprises about 15 to 35 weight percent orthoxylene.

10. In a process for the production of phosphorus-vanadium-zinc oxide catalyst in an organic reaction medium wherein the ratio of phosphorus to vanadium is in the range of about 1.2:1 to about 1.8:1 and the ratio of vanadium to zinc is in the ratio of about 0.001 to about 1:0.10, the improvement comprising adding $H_3PO_4$ immediately after the vanadium reduction has terminated and recycling mother liquor comprising at least 15 weight percent ortho xylene remainder being orthophosphoric acid and aliphatic alcohol and thus recovering up to ninety percent of the vanadium.

11. The process of claim 10, wherein the aliphatic alcohol is isobutyl alcohol.

12. The process of claim 10, wherein the mother liquor comprises about 15 to about 35 weight percent orthoxylene.

* * * * *

UNITED STATES PATENT OFFICE
CERTIFICATE OF CORRECTION

Patent No. 4,434,244     Dated February 28, 1984

Inventor(s) KUHLMANN, GEORGE E. - HOOVER, STEPHEN V.

It is certified that error appears in the above-identified patent and that said Letters Patent are hereby corrected as shown below:

| Column | Line  |           |           |             |
|--------|-------|-----------|-----------|-------------|
| 1      | 66    | "Suitable"| should be | --Suitably,--|
| 4      | 38-39 | "samples" | should be | --examples-- |
| 6      | 25    | "stirring"| should be | --starting-- |
| 8      | 52    | "1:0,10"  | should be | --1:0.10--   |

Signed and Sealed this

Twenty-fifth Day of June 1985

[SEAL]

Attest:

DONALD J. QUIGG

Attesting Officer    Acting Commissioner of Patents and Trademarks